(12) United States Patent
Montgomery et al.

(10) Patent No.: US 8,976,365 B2
(45) Date of Patent: *Mar. 10, 2015

(54) INTERFEROMETRIC MATERIAL SENSING APPARATUS INCLUDING ADJUSTABLE COUPLING AND ASSOCIATED METHODS

(71) Applicant: Harris Corporation, Melbourne, FL (US)

(72) Inventors: Robert M. Montgomery, Indialantic, FL (US); Randy L. Carmean, Malabar, FL (US); Charles Franklin Middleton, IV, Rockledge, FL (US); James G. Tonti, Palm Bay, FL (US)

(73) Assignee: Harris Corporation, Melbourne, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/108,540

(22) Filed: Dec. 17, 2013

(65) Prior Publication Data

US 2015/0009506 A1 Jan. 8, 2015

Related U.S. Application Data

(62) Division of application No. 13/102,686, filed on May 6, 2011, now Pat. No. 8,649,022.

(51) Int. Cl.
*G01B 11/02* (2006.01)
*G01B 9/02* (2006.01)

(52) U.S. Cl.
USPC .......................................... 356/502; 356/482

(58) Field of Classification Search
CPC .............. A61B 5/1075; A61B 5/6886; A61B 2562/0233; A61B 2562/223; A61B 5/0084; G01B 9/0205; G01B 9/02068; G01B 11/0666; G01B 9/02049; G01H 9/004; G01H 9/006; G01H 9/008; G01N 29/043; G01N 29/2418; G01N 9/00; G01N 21/1717; G01N 2291/02475
USPC ............. 356/480, 482, 502, 505, 506; 73/655
See application file for complete search history.

(56) References Cited

U.S. PATENT DOCUMENTS 4,180,324 A 12/1979 Primbsch
4,928,527 A 5/1990 Burger et al.
(Continued)

FOREIGN PATENT DOCUMENTS

EP 1498690 1/2005

OTHER PUBLICATIONS

Neubrand et al. "Laser Generation and Detection of Surface Acoustic Waves: Elastic Properties of Surface Layers", J. Appl. Phys. 71, 227, Jan. 1992, pp. 227-238.

(Continued)

*Primary Examiner* — Michael A Lyons
(74) *Attorney, Agent, or Firm* — Allen, Dyer, Doppelt, Milbrath & Gilchrist, P.A.

(57) ABSTRACT

A material sensing apparatus comprises an excitation source configured to induce waves in a workpiece, and an optical waveguide interferometer configured to sense the induced waves in the workpiece. The optical waveguide interferometer comprises a probe segment having a probe segment end, and an adjustable coupler configured to permit setting a gap between the probe segment end and the workpiece. A controller is coupled to the adjustable coupler and configured to set the gap between the probe segment end and the workpiece.

11 Claims, 14 Drawing Sheets

(56) References Cited

U.S. PATENT DOCUMENTS

| | | | |
|---|---|---|---|
| 5,684,592 A | 11/1997 | Mitchell et al. | |
| 6,008,887 A | 12/1999 | Klein et al. | |
| 6,075,603 A | 6/2000 | O'Meara et al. | |
| 6,188,050 B1 | 2/2001 | Duffer et al. | |
| 6,396,605 B1 | 5/2002 | Heflinger et al. | |
| 6,529,444 B2 | 3/2003 | Vakoc | |
| 6,542,245 B2 | 4/2003 | Toida | |
| 6,609,425 B2 | 8/2003 | Ogawa | |
| 6,819,432 B2 | 11/2004 | Pepper et al. | |
| 6,838,660 B2 | 1/2005 | Duncan et al. | |
| 6,839,496 B1 | 1/2005 | Mills | |
| 7,027,161 B2 | 4/2006 | Pepper | |
| 7,242,480 B2 | 7/2007 | Alphonse | |
| 7,262,861 B1 | 8/2007 | Pepper et al. | |
| 7,519,253 B2 | 4/2009 | Islam | |
| 7,728,967 B2 | 6/2010 | Ochiai et al. | |
| 8,144,334 B2 | 3/2012 | Chinn et al. | |
| 8,199,318 B2 | 6/2012 | Conner et al. | |
| 8,665,451 B2 * | 3/2014 | Montgomery et al. | 356/502 |
| 2011/0284508 A1 | 11/2011 | Miura et al. | |
| 2012/0281227 A1 | 11/2012 | Montgomery et al. | |
| 2012/0281228 A1 | 11/2012 | Montgomery et al. | |
| 2012/0281229 A1 | 11/2012 | Montgomery et al. | |
| 2012/0281230 A1 | 11/2012 | Montgomery et al. | |
| 2012/0281231 A1 | 11/2012 | Montgomery et al. | |
| 2012/0281232 A1 | 11/2012 | Montgomery et al. | |

OTHER PUBLICATIONS

Glorieux et al. "Surface Acoustic Wave Depth Profiling of Elastically Inhomogeneous Materials". J. Appl. Phys. 88, 4394, Oct. 2000, pp. 4394-4400.

Park et al. "Detection of Laser-Generated Ultrasound Based on Phase Demodulation Technique Using a Fibre Fabry-Perot Interferometer", Measurement Science and Technology, 2005, pp. 1261-1266.

Wang et al. "A Remote, Non-Destructive Laser Ultrasonic Material Evaluation System With Simplified Optical Fibre Interferometer Detection", J Nondestruc Eval. 28, Jun. 2009, pp. 75-83.

* cited by examiner

INTERFEROMETRIC MATERIAL SENSING APPARATUS INCLUDING ADJUSTABLE COUPLING AND ASSOCIATED METHODS

GOVERNMENT CONTRACT

This invention was made with Government support under Government Contract 03-180 awarded by the FBI. The Government has certain rights in this invention.

FIELD OF THE INVENTION

The present invention relates to the field of interferometers and, more particularly, to optical waveguide interferometers and related methods.

BACKGROUND OF THE INVENTION

Ultrasonic waves may be used to probe a variety of materials, particularly for thickness gauging and flaw detection. The ultrasonic waves are typically generated with a piezoelectric transducer. The ultrasonic waves propagate through the material, reflecting from interfaces (in thickness gauging applications) or internal features (in flaw detection applications). The scattered ultrasonic waves propagate back to the surface of the material, causing the surface to vibrate at the ultrasound frequency. This vibration may be detected with a piezoelectric transducer similar to the one used to generate the ultrasonic waves, and then analyzed to generate data about the material.

Optical detection techniques can be used in place of the piezoelectric transducers to remotely detect the ultrasonic waves. Generally, a laser probe beam is directed onto the material. When the surface vibrates it imparts a phase shift onto the reflected beam. This phase shift is detected with a photodetector after mixing the reflected probe beam with a stable reference beam and measuring the amplitude and frequency or phase of the photodetector output intensity fluctuations. The reference beam originates from the same laser source as the reflected probe beam, and the output signal from the photodetector corresponds to the surface motion.

One problem with laser detection systems is low sensitivity. Typically, the material surface that is being probed has a diffusely reflecting or scattering quality. Consequently, the reflected beam is highly aberrated and its wavefront is mismatched with respect to the reference beam. The resulting signal produced by the photodetector is therefore weak and lacks precision.

In U.S. Pat. No. 6,075,603 to O'Meara, a contactless system for imaging an acoustic source within a workpiece is disclosed. In this system, an array of discrete optical detectors is arranged in a pattern. A probe beam is directed onto a vibrating surface in a pattern that corresponds to the detector array. The probe beam is reflected onto the detector array and a reference beam is also directed onto the detector array at an angle to the probe beam to produce fringe patterns on the detectors that correspond to the surface vibration pattern. A readout system utilizes the discrete detector outputs to produce an array output signal indicative of at least a size and two dimensional location for the acoustic source relative to the vibrating surface. This system, however, may not provide the desired accuracy, and may be sensitive to fluctuations in the length of the paths between the probe beam and the surface, and the reference beam and the surface.

U.S. Pat. No. 7,262,861 to Pepper discloses a laser ultrasonic inspection apparatus which enables remote sensing of thickness, hardness, temperature and/or internal defect detection. A laser generator impinges on a workpiece with light for generating a thermo-elastic acoustic reaction in a workpiece. A probe laser impinges on the workpiece with an annularly-shaped probe light for interaction with the acoustic signal in the workpiece resulting in a modulated return beam. A photodetector having a sensitive region is used for detecting an annularly-shaped fringe pattern generated by an interaction of a reference signal with the modulated return beam at the sensitive region.

This system, however, may not provide the desired accuracy, and may be sensitive to fluctuations in the length of the path between the probe beam and the surface, or fluctuations in the path lengths of the reference and measurement arms of the interferometer.

SUMMARY OF THE INVENTION

In view of the foregoing background, it is therefore an object of the present invention to provide a biological material sensing apparatus. This and other objects, features, and advantages in accordance with the present invention are provided by a biological material sensing apparatus permitting adjustment of a gap between an interferometer probe and a workpiece that includes an excitation source configured to induce waves in a workpiece, and an optical waveguide interferometer configured to sense the induced waves in the workpiece. The optical waveguide interferometer comprises a probe segment having a probe segment end, and an adjustable coupler configured to permit setting a gap between the probe segment end and the workpiece. A controller is coupled to the adjustable coupler and configured to set the gap between the probe segment and the workpiece.

The optical waveguide interferometer may also include a laser source, and a photodetector coupled to the controller. An optical coupler operatively connects the laser source, the photodetector, and the probe segment. The controller is further configured to generate workpiece data based upon the sensed induced waves.

Setting the gap between the probe segment and the workpiece advantageously allows the optical waveguide interferometer to be tuned such that the distance between the probe segment end and the workpiece is a desired fraction or multiple of the wavelength of light emitted from the probe segment end. This helps to minimize distortions in the generated workpiece data.

In some applications, the adjustable coupler may comprise a piezoelectric body. Alternatively, the adjustable coupler may comprise a sleeve surrounding the probe segment end and at least one of a heating source and a cooling source associated therewith. In some applications, the heating source may be a laser.

The adjustable coupler comprises a sleeve surrounding the probe segment end. In addition, the adjustable coupler may further comprise a biasing member configured to urge the sleeve in contact with the workpiece. The probe end comprises an optical fiber with an angled endface, and the excitation source may comprise at least one pulsed laser.

A method aspect is directed to a method of sensing a workpiece comprising inducing waves in the workpiece using an excitation source, and sensing the induced waves in the workpiece using an optical waveguide interferometer comprising a probe segment end by at least setting a gap between the probe segment end and the workpiece.

According to another aspect, a biological material sensing apparatus comprises an excitation source configured to induce waves in a workpiece, and an optical waveguide interferometer configured to sense the induced waves in the workpiece. The optical waveguide interferometer comprises a laser source, and a probe segment having a probe segment end to be positioned adjacent the workpiece and defining a gap therebetween. An optical coupler is operatively connecting the laser source and the probe segment. In addition, a controller is coupled to the laser source and configured to adjust the wavelength of the laser source so that a desired multiple of the wavelength equals the gap between the probe segment end and the workpiece.

According to a further aspect, a biological material sensing apparatus includes an excitation source configured to induce waves in a workpiece, and an optical waveguide interferometer configured to sense the induced waves in the workpiece. The optical waveguide interferometer comprises a laser source, and a probe segment having a probe segment end to be positioned adjacent the workpiece and defining a gap therebetween. An optical coupler operatively connects the laser source and the probe segment, and a controller is coupled to the laser source and configured to adjust the wavelength of the laser source so that a desired multiple of the wavelength equals the gap between the probe segment end and the workpiece.

BRIEF DESCRIPTION OF THE DRAWINGS

FIG. 11 is a schematic block diagram of yet another sensing apparatus in accordance with the present invention.

DETAILED DESCRIPTION OF THE PREFERRED EMBODIMENTS

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout, and prime and multiple prime notations are used to indicate similar elements in alternative embodiments.

Figure 1:
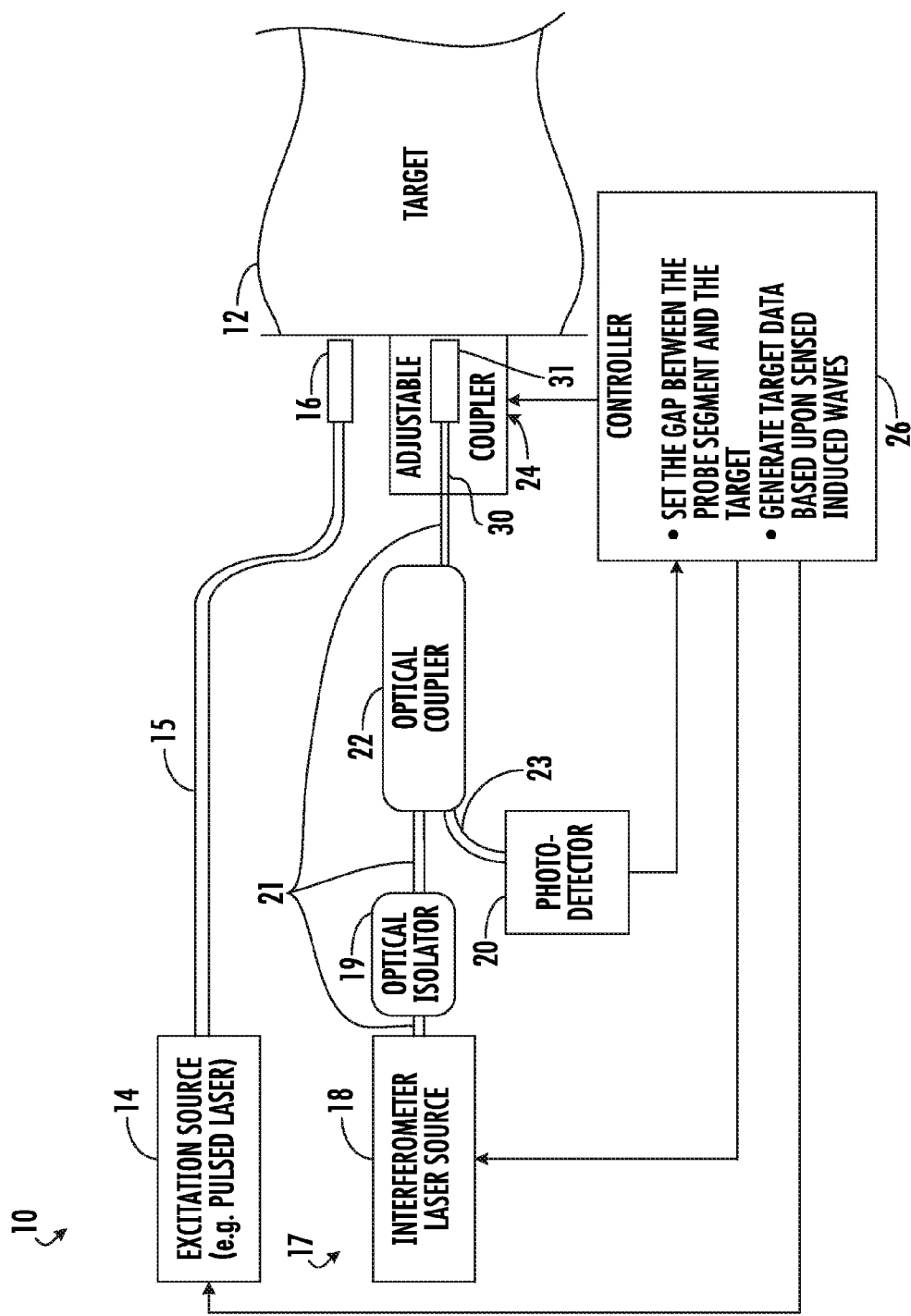
FIG. 1 is a schematic block diagram of a sensing apparatus, according to the present invention.

Referring initially to FIG. 1, a sensing apparatus 10 in accordance with the present invention is now described. The sensing apparatus 10 is used to sense, or determine, a variety of properties of a target 12, including, for example, the dimensions of the target, the material composition of the target, and the thickness of the target.

The sensing apparatus 10 includes an excitation source 14, illustratively a pulsed laser, configured to induce ultrasonic waves in the target 12. The excitation source 14 is an optical source and is illustratively coupled to the target 12 via an optical fiber 15 having an end portion 16 in physical contact with the target, although it should be appreciated that in some embodiments the excitation source is not coupled to the target via an optical fiber but rather radiates the target via free space. The excitation source 14 induces the ultrasonic waves in the target 12 by rapidly heating it. It should be appreciated that in some applications, the excitation source 14 may be a broadband optical source, or a doped fiber amplifier.

An optical waveguide interferometer 17 senses the induced waves and generates target data based thereupon. In particular, the optical waveguide interferometer 17 comprises a probe segment 30 having a probe segment end 31 coupled to the target 12. The interferometer laser source 18 is connected to an adjustable coupler 14 via optical fibers 21 and through an optical isolator 19 and an optical coupler 22. Also coupled to the optical coupler 22 is a photo-detector 20 via optical fiber 23.

The adjustable coupler 24 is in physical contact with the target 12, and permits setting a gap between the probe segment end 31 and the target. A controller 26 is coupled to the adjustable coupler 24 and is configured to control the adjustable coupler to thereby set the gap between the probe segment end 31 and the target 12.

Operation of the optical waveguide interferometer 17 is now described. The interferometer laser source 18 radiates the target 12 via the probe segment end 31. A portion of the light radiating within the probe segment 30 is reflected back as it hits the probe segment end 31, through the optical coupler 22, and into the photodetector 20. Similarly, a portion of the light radiating within the probe segment 30 is radiated from the probe segment end 31 onto the target 12. This light is then reflected from the target 12 back into the probe segment 30 via the probe segment end 31, through the optical coupler 22, and into the photodetector 20. Consequently, the light reflected from the probe segment end 31 and the light reflected from the target 12 will combine, and the superposition thereof is detected by the photodetector 20. The light reflected by the target will typically undergo a phase change due to the ultrasonic waves and resulting vibrations in the target 12, and therefore will have a different phase than the light reflected by the probe segment end 31, causing constructive and destructive interference to occur therebetween. This interference therefore reflects a detection of the sensed induced waves and can be analyzed in order to determine various properties of the target, as will be appreciated by those skilled in the art.

The controller 26 generates target data based upon the sensed induced waves. To do so, a laser pulse from the pulsed laser 14 triggers the start of a measurement cycle, performed by the controller 26, in the time domain. Signal peaks observed by the controller 26 correspond to the transit time of surface waves from the point of excitation (that is, the point of the target 12 on which the pulse from the pulsed laser 14 radiates) to the probe segment end 31. Since the distance between the excitation point and the probe segment end 31 is known, the acoustic velocity of the ultrasonic waves in the target 12 can be calculated. By comparing this acoustic velocity to a table of acoustic velocity for different materials, the material composition of the target can be determined. It should be understood that the adjustable coupler 24 and excitation source probe 16 can be scanned to different locations on the target 12, so as to gather information about many points of the target.

The controller 26 may include a processor and a memory cooperating therewith. The memory may be volatile or nonvolatile, and the processor may be an integrated circuit, in some applications.

In addition, the controller 26 performs typical interferometric calculations as known to those of skill in the art on the superposition of the light reflected by the probe segment end 31 and the light reflected by the target 12 to potentially determine the dimensions and/or the thickness of the target. Since a difference in the length of the path traveled by the light reflected by the probe segment end 31 and the light reflected by the target 12 will result in an additional phase difference therebetween, it is desirable for the difference in the length of that path to remain the same. That is, it desirable for the gap between the probe segment end 31 and the target 12 to remain constant, such that the gap is a desired multiple of the wavelength of the light radiated by, and reflected into, the probe segment end 31'. The multiple used need not be an integer in some embodiments, and need not be greater than one in some embodiments.

Figure 2:
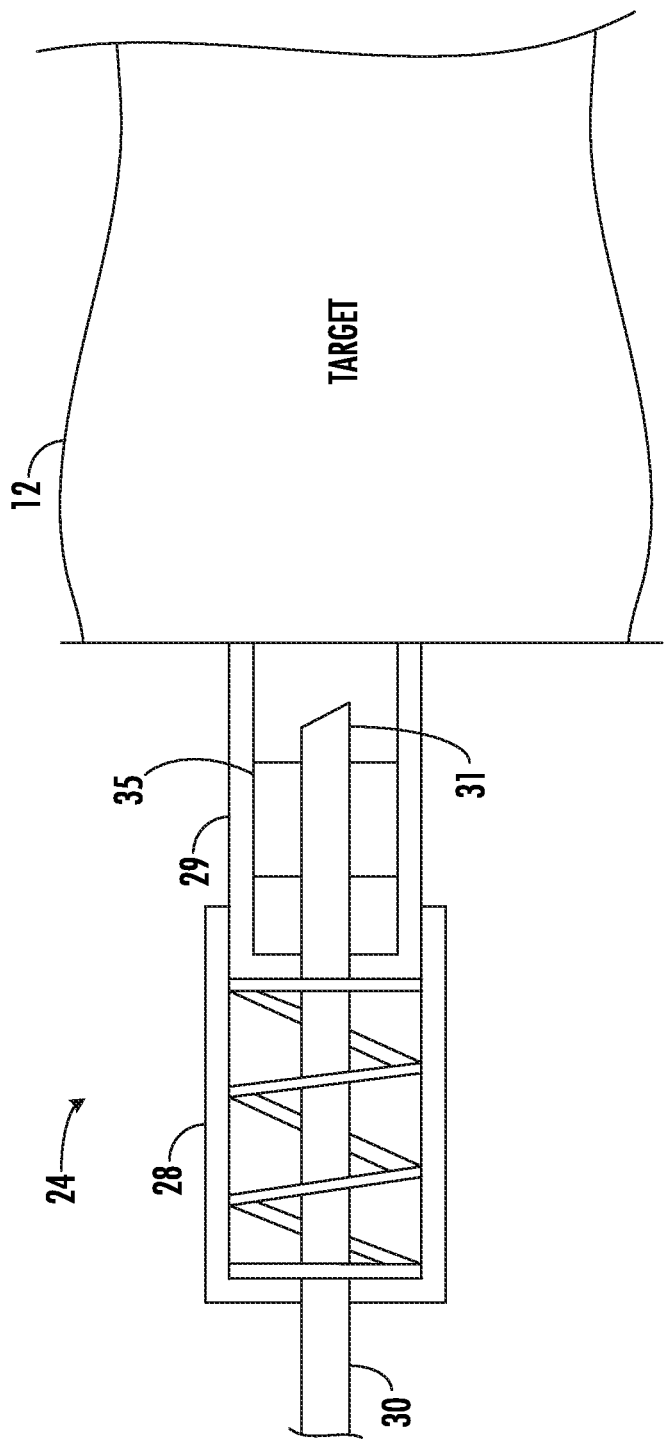
FIG. 2 is a schematic sectional view of an adjustable coupler, as used with the sensing apparatus of FIG. 1.

As stated above, the controller 26 controls the adjustable coupler 24 to adjust the gap. As shown in FIG. 2, the adjustable coupler 24, in some embodiments, may comprise a sleeve 29 surrounding probe segment end 31, and a biasing member 28 to urge the sleeve 29 in physical contact with the target 12. The biasing member 28 comprises a cylinder configured to receive the sleeve 29, and a spring arranged so as to urge the sleeve in contact with the target 12. A ferrule 35 slidably holds the probe segment end 31 inside the sleeve 29. The purpose of the biasing member 28 urging the sleeve 29 in contact with the target 12 is to help coarsely adjust the gap between the probe segment end 31 and the target 12 even though the target may be vibrating.

Thermal drifting, however, may cause the sleeve 29, the probe 30, and the probe segment end 31 to expand and contract at different rates, which leads to the gap changing. Since this is not desirable, the adjustable coupler 24 may include additional components to fine tune the gap.

Figure 3:
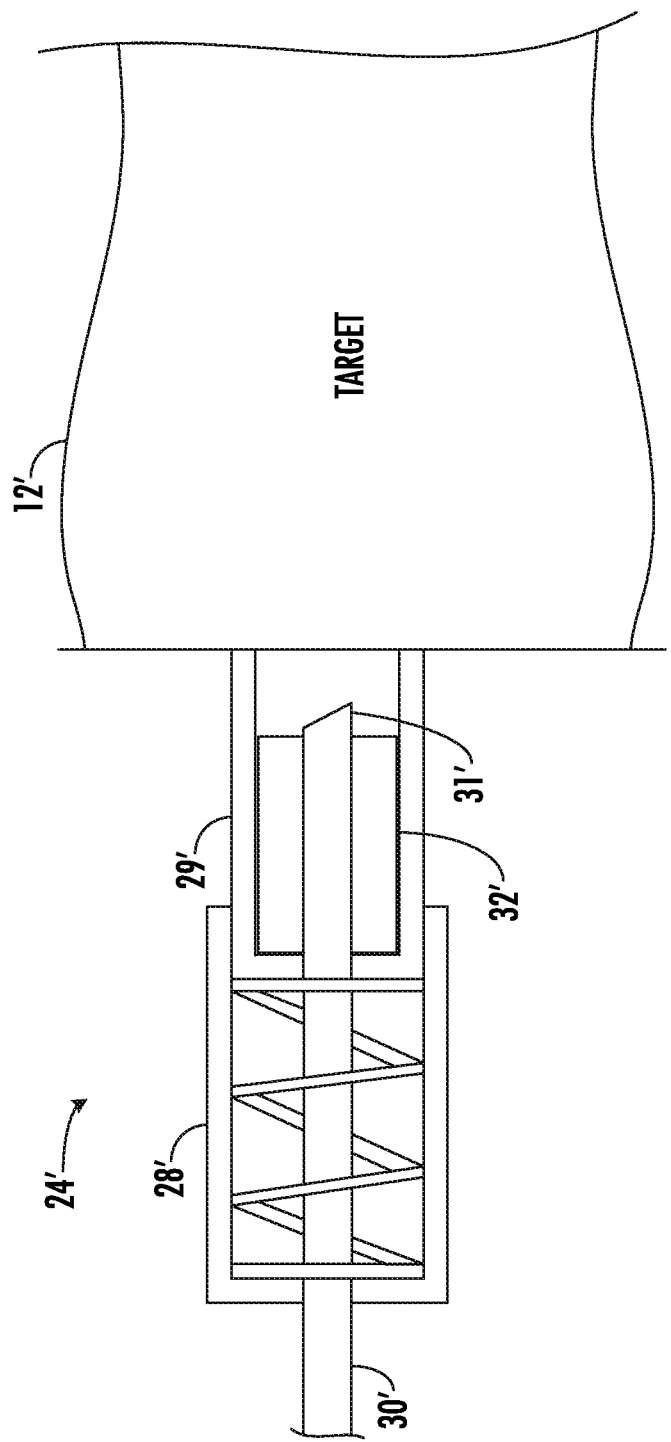
FIG. 3 is a schematic sectional view of another adjustable coupler, such as may be used with the sensing apparatus of FIG. 1.

For example, as shown in FIG. 3, the adjustable coupler 24' may include a piezoelectric sleeve 32' surrounding the probe segment end 32', which is in turn surrounded by the sleeve 29'. The controller 26' applies a voltage to the piezoelectric sleeve 32', causing the piezoelectric sleeve to expand or contract, thereby altering the length of the probe segment end 31'. This therefore allows fine tuning of the gap between the probe segment end 31' and the target 12'. The controller 26' may be coupled to the piezoelectric sleeve 32' via any suitable method, such as suitable electrical contacts between the sleeve 29' and the piezoelectric sleeve 32'.

Figure 4:
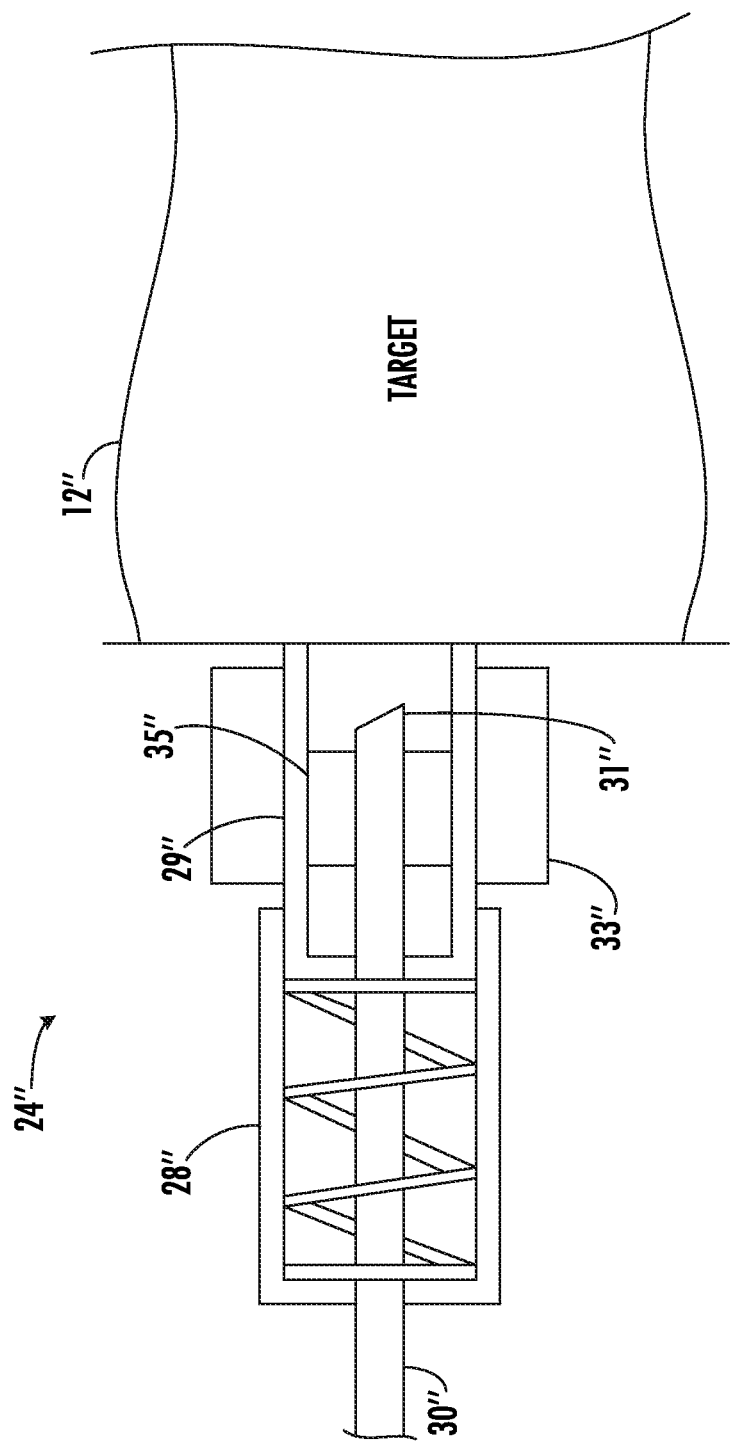
FIG. 4 is a schematic sectional view of yet another adjustable coupler, such as may be used with the sensing apparatus of FIG. 1.

Another embodiment of the adjustable coupler 24 is shown in FIG. 4, and includes a temperature control unit 33" surrounding the sleeve 29". The temperature control unit 33" is illustratively a Peltier effect unit, and is controlled by the controller 26". The controller 26" uses the Peltier effect unit 33" to heat or cool the sleeve 29" and probe segment end 31" to thereby cause the sleeve 29" and probe segment end 31" to expand or contract, which in turn allows fine tuning of the gap between the probe segment end and the target 12".

Figure 5:
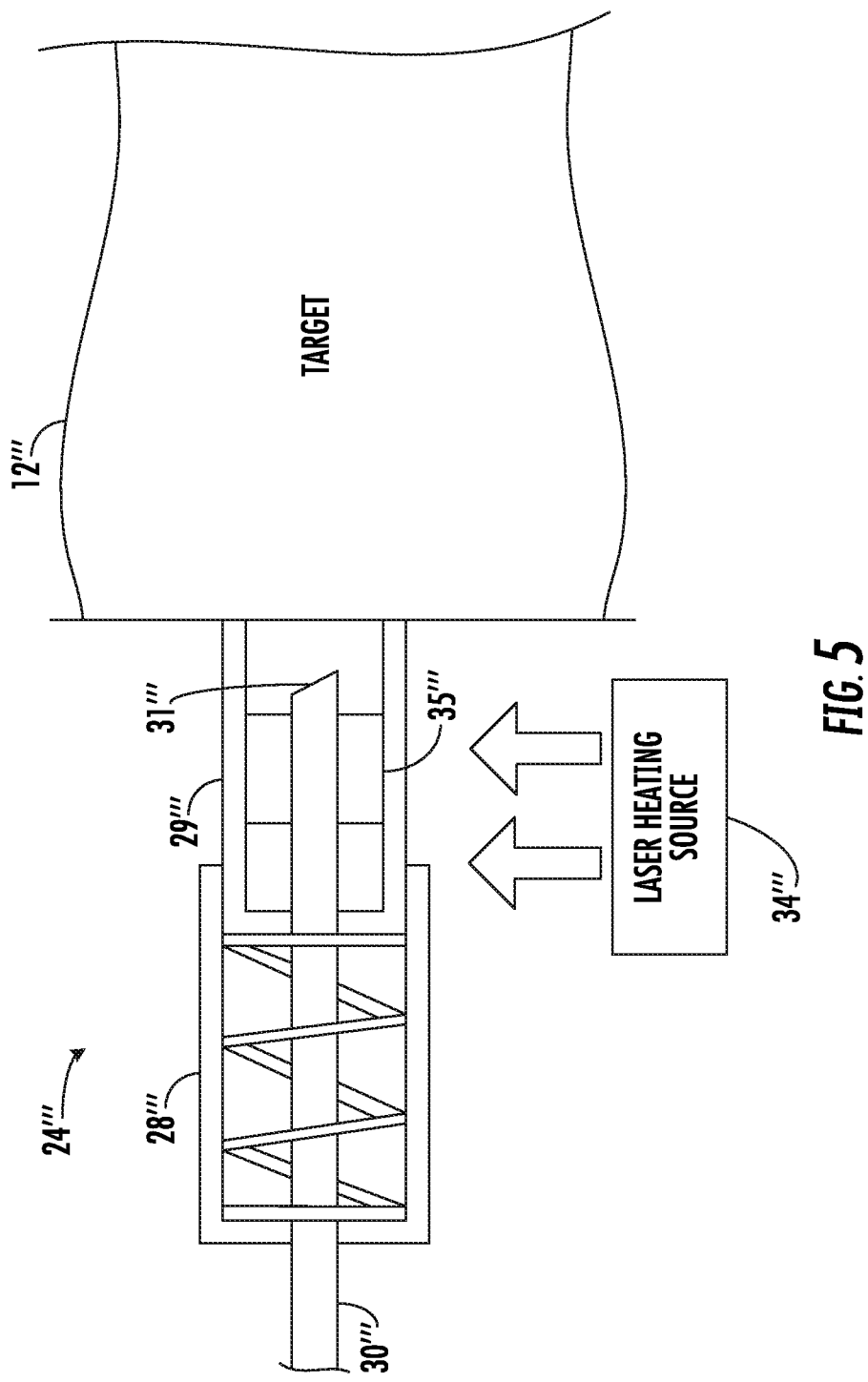
FIG. 5 is a schematic cross sectional view of an additional adjustable coupler, such as may be used with the sensing apparatus of FIG. 1.

A further embodiment of the adjustable coupler 24''' is shown in FIG. 5, and includes a laser heating source 34''' configured to radiate the sleeve 29''', and thereby heat the sleeve 29''' and probe segment end 31" to cause the sleeve and probe segment end to expand or contract, which in turn allows fine tuning of the gap between the probe segment end and the target 12".

Referring once again to FIG. 1, in the above examples, it should be understood the controller 26 controls the adjustable coupler 24 based upon an error signal. This error signal may be the DC component of the light detected by the photodetector 20, for example.

Figure 6:
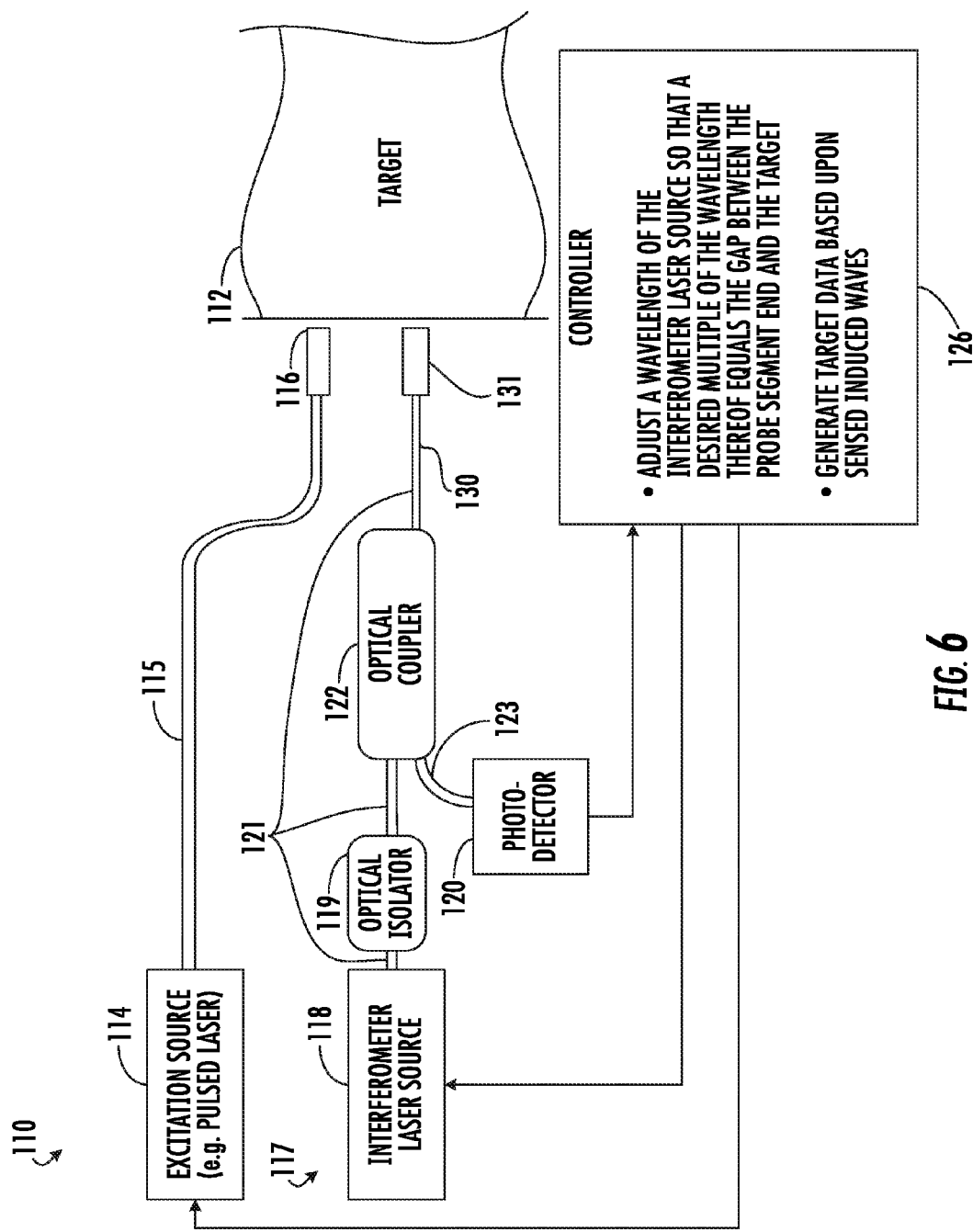
FIG. 6 is a schematic block diagram of another embodiment of a sensing apparatus, according to the present invention.

A further embodiment of the sensing apparatus 110 is shown in FIG. 6. Here, there is no mechanically adjustable coupler, although the excitation source 114, optical fiber 115 having an end portion 116, optical isolator 119, optical coupler 122, photodetector 120, optical fiber 123, probe segment 130, probe segment end 131, and optical fibers 115, 121 are similar to those described above with reference to FIG. 1. Rather than adjusting the gap between the probe segment end 131 and the target 112 such that the gap is a desired multiple of the wavelength of the light radiated by, and reflected into, the probe segment end, the wavelength of the interferometer laser source 118 is adjusted by the controller 126 such that a desired multiple of the wavelength equals the gap.

It should be understood that the sensing apparatuses 10, 10', 10", 10''', 110 disclosed above may include an array of excitation sources 14, 14', 14", 14''', 114, and an array of optical waveguide interferometers 18, 18', 18", 18''', 118.

Figure 7:
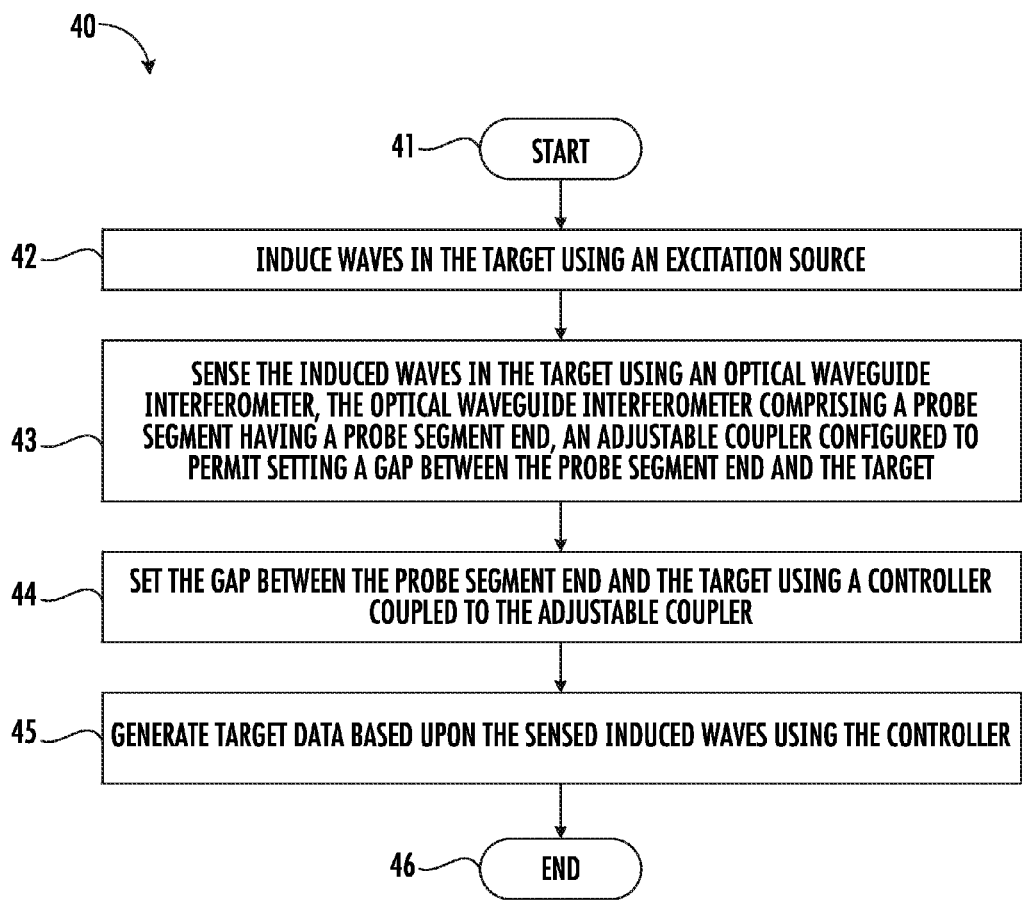
FIG. 7 is a flowchart of a method of sensing a target in accordance with the present invention.

With additional reference to the flowchart 40 of FIG. 7, a method of sensing a target is now described. After the start (Block 41), waves are induced in a target by an excitation source (Block 42). Next, the induced waves are sensed by an optical waveguide interferometer (Block 43). The optical waveguide interferometer comprises a probe segment having a probe segment end, an adjustable coupler configured to permit setting a gap between the probe segment end and the target.

Next, the method includes setting the gap between the probe segment end and the target using a controller coupled to the adjustable coupler (Block 44). Then, target data is generated based upon the sensed induces waves, using the controller (Block 45). Block 46 indicates the end of the method.

It should be understood that the sensing apparatuses 10, 10', 110 disclosed above offer numerous advantages. For example, the use of a pulsed laser 14, 14', 114 as an excitation source allows a wide bandwidth of ultrasonic waves to be induced in the target 12, 12', 112 as opposed to conventional piezoelectric excitation sources which typically produce more narrow bandwidths. For example, the pulsed laser 14, 14', 114 can produce ultrasonic waves with a bandwidth above 1 MHz, which is difficult to achieve with conventional piezoelectric excitation sources. In addition, with a piezoelectric excitation source, a physical matching layer of often required to achieve a proper acoustic impedance match between the excitation source and the target. The sensing apparatuses 10, 10', 110 disclosed above do not suffer this drawback and are adaptable to a wide range of target materials by adjusting the interferometer spacing either through tuning of the interferometer laser 18, 18', 118 wavelength, or tuning of the adjustable coupler 24, 24', 124', as opposed to using a variety of matching layers.

In addition, the ability of the sensing apparatuses 10, 10', 10", 10''' to either adjust the gap between the probe segment end 31, 31', 31", 31''' and the target 12, 12', 12", 12''' or the wavelength of the interferometer laser source 118, on the fly and based upon a feedback error signal provides for precise results, as effects that negatively impact the results can be adjusted for and mitigated. Furthermore, the use of a pulsed laser 14, 14', 14", 14''', 114 as the excitation source, coupled with the use of the optical waveguide interferometer 17, 17', 17", 17''', 117 allows the sensing apparatus 10, 10', 10", 10''', 110 to be compact and portable. Moreover, the use of optical fibers to couple the pulsed laser 14, 14', 14", 14''', 114 and interferometer laser source 18, 18', 18", 18''', 118 to the target 12, 12', 12", 12''', 112 allows the sensing of hard to reach targets, since the optical fibers may be inserted into small spaces.

Figure 8:
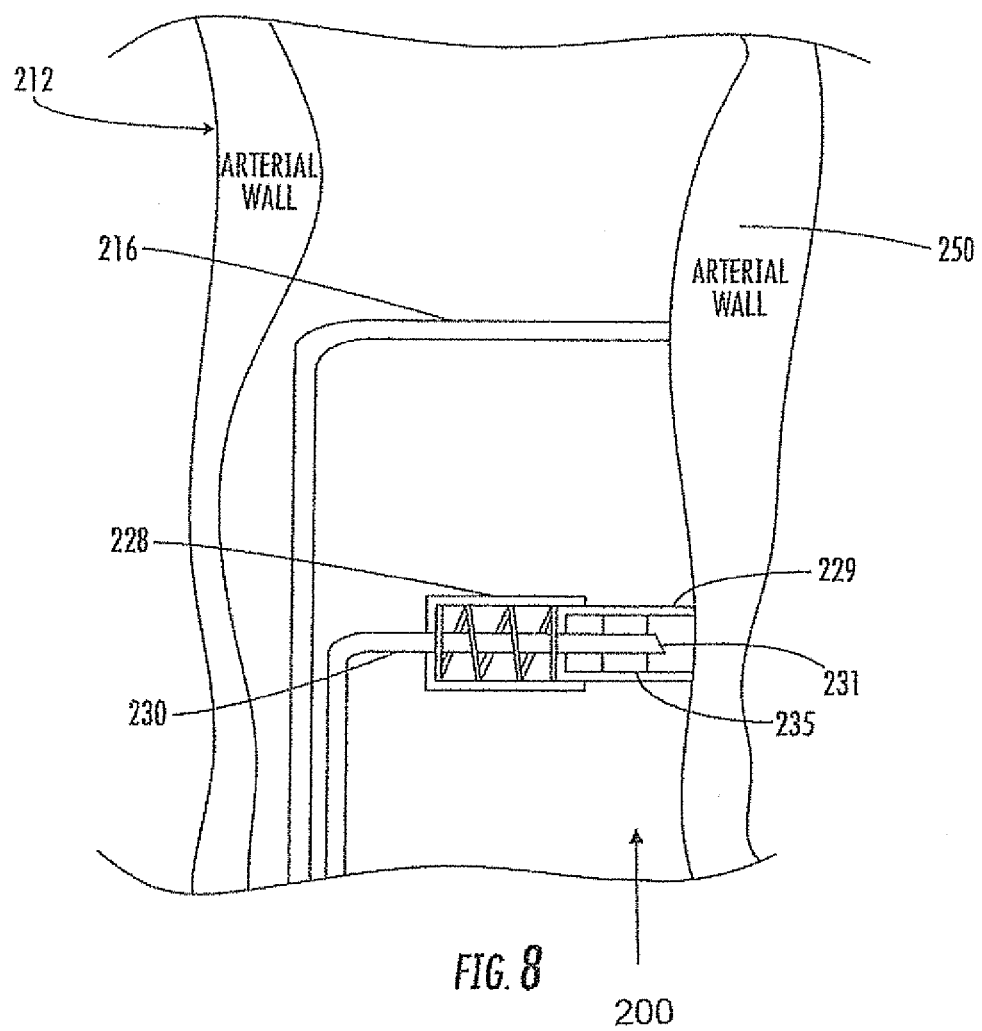
FIG. 8 is a partial schematic sectional view of an adjustable coupler of a biological sensing apparatus sensing an arterial wall in accordance with the present invention.

The sensing apparatuses 10, 10', 10", 10''', 110 disclosed herein are useful in a wide variety of applications. For example, they may be useful in medical imaging systems, for sensing and imaging body parts. For example, the optical fibers of the pulsed laser 14, 14', 14", 14''', 114 and interferometer laser source 18, 18', 18", 18''', 118 may be inserted into arteries, in order to image those arteries or measure the thickness thereof, or may be inserted into a trachea in order to image various components of the digestive system of a patient. Shown in FIG. 8 is an embodiment where the sensing apparatus 200 (similar to the sensing apparatuses disclosed above) is a biological sensing device, and the target 212 is an artery having an arterial wall 250. Here, the controller will generate anatomical data about the arterial wall 250, such as a thickness or density of the arterial wall. Those skilled in the art will appreciate that any biological sample or body part may be sensed using this sensing apparatus 200. The illustrated reference numbers in FIG. 8 have been increased by 200 with respect to FIGS. 1 and 2 to indicate similar elements in alternative embodiments. Some of the reference numbers in FIG. 8 will not be discussed to simplify the discussion herein, as readily understood by those skilled in the art.

Figure 9:
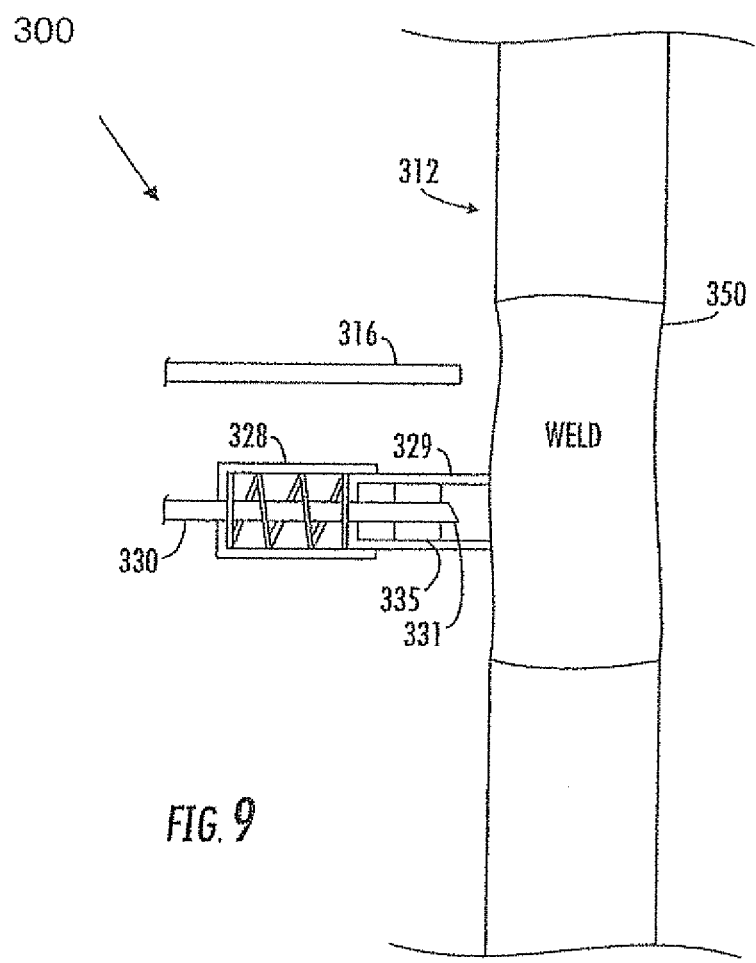
FIG. 9 is a partial schematic sectional view of an adjustable coupler of a material inspection apparatus sensing a weld in accordance with the present invention.

In addition, the sensing apparatuses 10, 10', 10", 10''', 110 may be used for materials inspection. For example, small welds, or welds in inaccessible places, may be inspected using the sensing apparatuses 10, 10', 10", 10''', 110. Wire bonds in electronic devices may be inspected using the sensing apparatuses 10, 10', 10", 10''', 110. Hydraulic lines, such as those used in avionics systems of aircraft, or brake lines of a motor vehicle, may be inspected using the sensing apparatuses 10, 10', 10", 10''', 110. Shown in FIG. 9 is an embodiment where the sensing apparatus 300 (similar to the sensing apparatuses disclosed above) is a material inspection device, and the target 312 is a workpiece having a weld 350 to be inspected. The illustrated reference numbers in FIG. 9 have been increased by 300 with respect to FIGS. 1 and 2 to indicate similar elements in alternative embodiments. Some of the reference numbers in FIG. 9 will not be discussed to simplify the discussion herein, as readily understood by those skilled in the art. Here, the controller will generate material data about the material weld 350, such as a thickness, density, or composition of the weld 350. Of course, this material inspection device 300 need not be limited to weld inspection and may be used to sense or inspect any sort of workpiece.

It should be understood that the specific use examples given above are by no means limiting, and that those of skill in the art will appreciate that the sensing apparatuses 10, 10', 10", 10''', 110 may be useful in an unlimited number of fields.

Figure 10:
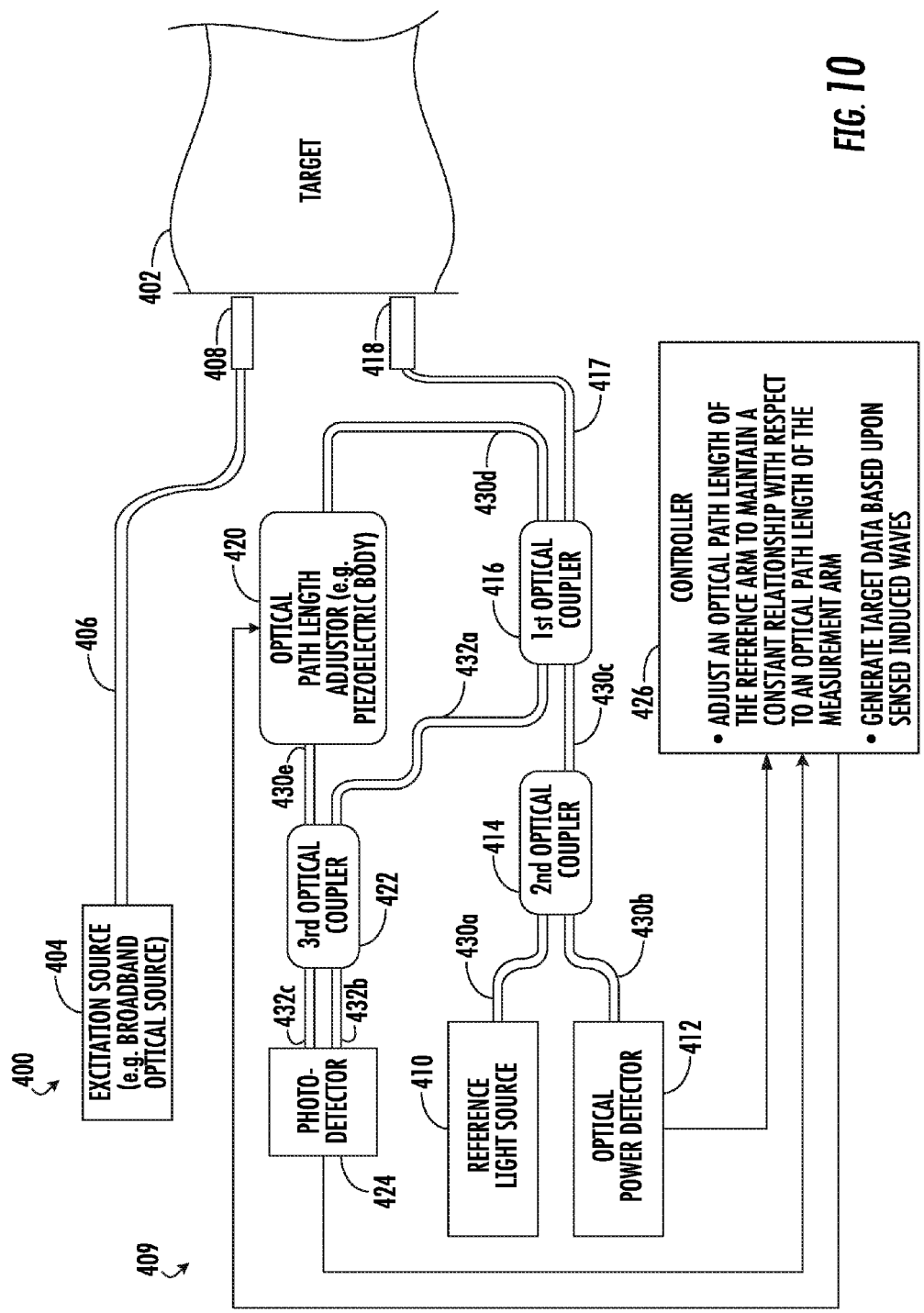
FIG. 10 is a schematic block diagram of another sensing apparatus in accordance with the present invention.
Figure 17:
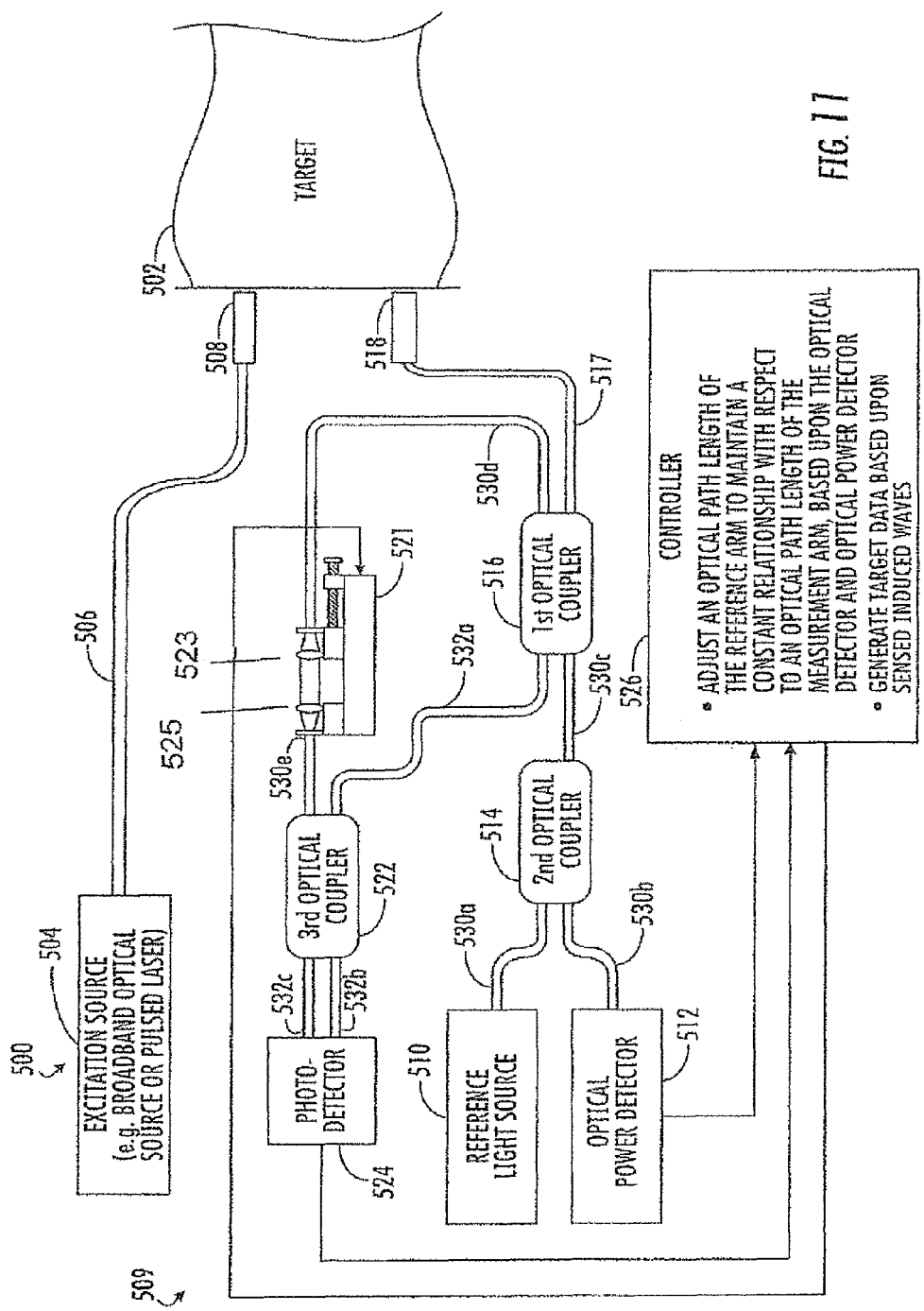

Referring to FIG. 10, another embodiment of a sensing apparatus 400 in accordance with the present invention is now described. The sensing apparatus 400 is used to sense, or determine, a variety of properties of a target 402, including, for example, the dimensions of the target, the material composition of the target, and the thickness of the target.

The sensing apparatus 400 includes an excitation source 404, illustratively a broadband optical source, configured to induce ultrasonic waves in the target 402. The excitation source 404 is an optical source and is illustratively coupled to the target 402 via an optical fiber 406 having an end portion 408 in physical contact with the target, although it should be appreciated that in some embodiments the excitation source is not coupled to the target via an optical fiber but rather radiates the target via free space. The excitation source 404 induces the ultrasonic waves in the target 402 by rapidly heating it. It should be appreciated that in some applications, the excitation source 404 may be a coherent optical source (e.g. a pulsed laser), or a doped fiber amplifier. In fact, in some applications, the excitation source 404 may be a pulsed laser having a spectral width that is inversely proportional to the pulse duration.

An optical waveguide interferometer 409 senses the induced waves and generates target data based thereupon. In particular, the optical waveguide interferometer 409 comprises a plurality of optical couplers 416, 414, 422 and interconnecting optical fibers 430a-430e, 432a-432c arranged to define a reference arm (430a-430e) and a measurement arm (432a-432c). A probe segment 417 is coupled to portions of the reference arm 430c, 430d and portions of the measurement arm 432a. As will be discussed in greater detail below, the optical fibers 430a-430e making up the reference arm allow reference light as well as input light and measurement light to travel. The probe segment 417 has a probe segment end 418 to be positioned adjacent the target 402b. An optical path length adjustor 420 is coupled to portions of the reference arm 430d, 430e. The optical path length adjustor 420 is illustratively a piezoelectric body, although it should be understood that any suitable optical path length adjustor or fiber stretcher may also be used.

A reference light source 410 is coupled to the reference arm 430a-430e and is configured to radiate light into the reference arm, and onto the target 402 via the probe segment end 418. The reference light source can be a laser source or doped fiber amplifier, as will be appreciated by those skilled in the art. For example, the reference light source may be a high gain erbium doped fiber amplifier with a 40 nm bandwidth, centered around a wavelength of 1550 nm.

An optical power detector 412 is coupled to the reference arm 430a-430e and is configured to receive light from the reference light source 410 reflected by the target 402 into the probe segment end 418.

The plurality of optical couplers 416, 414, 422 includes a first optical coupler 416 coupling portions of the reference arm 430c, 430d to portions of the measurement arm 432a and the probe segment 417. A second optical coupler 414 couples the first optical coupler 416 to the reference light source 410 and optical power detector 412. A third optical coupler 422 couples portions of the reference arm 430e to portions of the measurement arm 432a-432c, which thereby provides a differential output to the photodetector 424.

A controller 426 is coupled to the optical path length adjustor 420 and is configured to adjust an optical path length of the reference arm 430a-430e to maintain a constant relationship with respect to an optical path length of the measurement arm 432a-432c. The controller 426 may adjust the optical path length of the reference arm 430a-430e based upon the optical power detector 412 and/or the differential output provided to the photodetector 424.

Thermal drifting may cause the length of the optical fibers within the reference arm 430a-430e and the measurement arm 432a-432c to expand and contract at different rates, which leads to the change of their respective lengths. This is undesirable because it negatively affects the accuracy of the sensing apparatus 400. The controller 426 helps rectify this undesirable condition by adjusting the path length of the reference arm 430a-430e using the optical path length adjustor 420. The matching of the path length of the reference arm 430a-430e and the measurement arm 432a-432c by the controller 426 using the optical path length adjustor 420 to within 0.0025 in allows particularly accurate results.

Operation of the optical waveguide interferometer 409 is now described. A portion of the light radiated by the reference light source 410 is radiated from the probe segment end 418 onto the target 402. This light is then reflected from the target 402 back into the probe segment 417 via the probe segment end 418, through the first optical coupler 416, through the second optical coupler 414, and into the optical power detector 412. The optical power detector 412 measures the optical power reflected from the target 402, and due to the arrangement of the optical couplers 416, 414, 422, only the optical power reflected from the target. That is, the optical couplers 416, 414, 422 are arranged such that the light directly emitted by the reference light source 410 does not reach the optical power detector 412, and only the light reflected from the target 402 reaches the optical power detector.

A portion of the light radiating from the reference light source 410 is conducted through the reference arm 430a-430e by the arrangement of optical couplers 416, 414, 422 and to the photodetector. Consequently, the light reflected from the target 402 and a portion of the light radiated by the reference light source 410 and conducted through the reference arm 430a-430e will combine, and the superposition thereof is detected by the photodetector 424.

The light reflected by the target 402 will typically undergo a phase change due to the ultrasonic waves and resulting vibrations in the target, and therefore will have a different phase than the light radiated by the reference light source 410 and conducted through the reference arm 430a-430e, causing constructive and destructive interference to occur therebetween. This interference therefore reflects a detection of the sensed induced waves and can be analyzed in order to determine various properties of the target, as will be appreciated by those skilled in the art.

The controller 426 generates target data based upon the sensed induced waves. To do so, a pulse from the excitation source 404 triggers the start of a measurement cycle, performed by the controller 426, in the time domain. Signal peaks observed by the controller 426 correspond to the transmit time of surface waves from the point of excitation (that is, the point of the target 402 on which the pulse from the excitation source 404 radiates) to the probe segment end 418. Since the distance between the excitation point and the probe segment end 418 is known, the acoustic velocity of the ultrasonic waves in the target 402 can be calculated. By comparing this acoustic velocity to a table of acoustic velocity for different materials, the material composition of the target can be determined. It should be understood that the excitation source probe 408 and probe segment end 418 can be scanned to different locations on the target 402, so as to gather information about many points of the target.

The controller 426 may include a processor and a memory cooperating therewith. The memory may be volatile or non-volatile, and the processor may be an integrated circuit, in some applications.

In addition, the controller 426 performs typical interferometric calculations as known to those of skill in the art on the superposition of the light radiated from the reference light source 410 and directed through the reference arm 430a-430e and the light reflected by the target 402 to potentially determine the dimensions and/or the thickness of the target.

Since a difference in the length of the path traveled by the light reflected by the probe segment end 418 and the light radiated from the reference light source 410 and directed through the reference arm 430a-430e will result in an additional phase difference therebetween, it is desirable for the length of the reference arm 430a-430e and the length of the measurement arm 432a-432c to remain the same, or at least for a constant relationship between the length of the reference arm and measurement arm to be maintained. If a constant relationship between the length of the reference arm 430a-430e and the measurement arm 432a-432c is to be maintained, it is desirable for the difference in length to be a desired multiple of the wavelength of the light radiated by reference light source 410. The multiple used need not be an integer in some embodiments, and need not be greater than one in some embodiments.

It should be appreciated that the optical path length adjustor 420 need not operate by physically changing a length of an optical fiber in all embodiments. For example, the optical path length adjustor 420 may be an adjustable delay line or phase modulator which can maintain a constant phase relationship between the light reflected from the target 402 and the light radiated by the reference light source 410 and through the reference arm 430a-430e. The maintenance of a constant phase relationship between the light in the reference arm 430a-430e and the measurement arm 432a-432c also helps to provide accurate results.

In some applications, the reference arm 430a-430e may even include a free space element. One such embodiment is now described with reference to FIG. 11. The illustrated reference numbers in FIG. 11 have been increased by 100 with respect to FIG. 10 to indicate similar elements in alternative embodiments. Some of the reference numbers in FIG. 11 will not be discussed to simplify the discussion herein, as readily understood by those skilled in the art. Here, the sensing apparatus 500 remains the same as the sensing apparatus 400 of FIG. 10, except that the reference arm 530a-530e includes a free space element. Here, the free space element is contained within an adjustable lens arrangement 521. The reference optical fiber 530d terminates at a coupler on the first side of the adjustable lens arrangement 521, and radiates reference light via free space and through a first lens 523. The reference light then passed through a second lens 525, which focuses the light back into the reference optical fiber 530e via another coupler. The distance between the first lens 523 and second lens 525 is adjustable based upon input received from the controller 526. This thereby allows adjustment of the length of the path of the reference arm 530a-530e.

Figure 12:
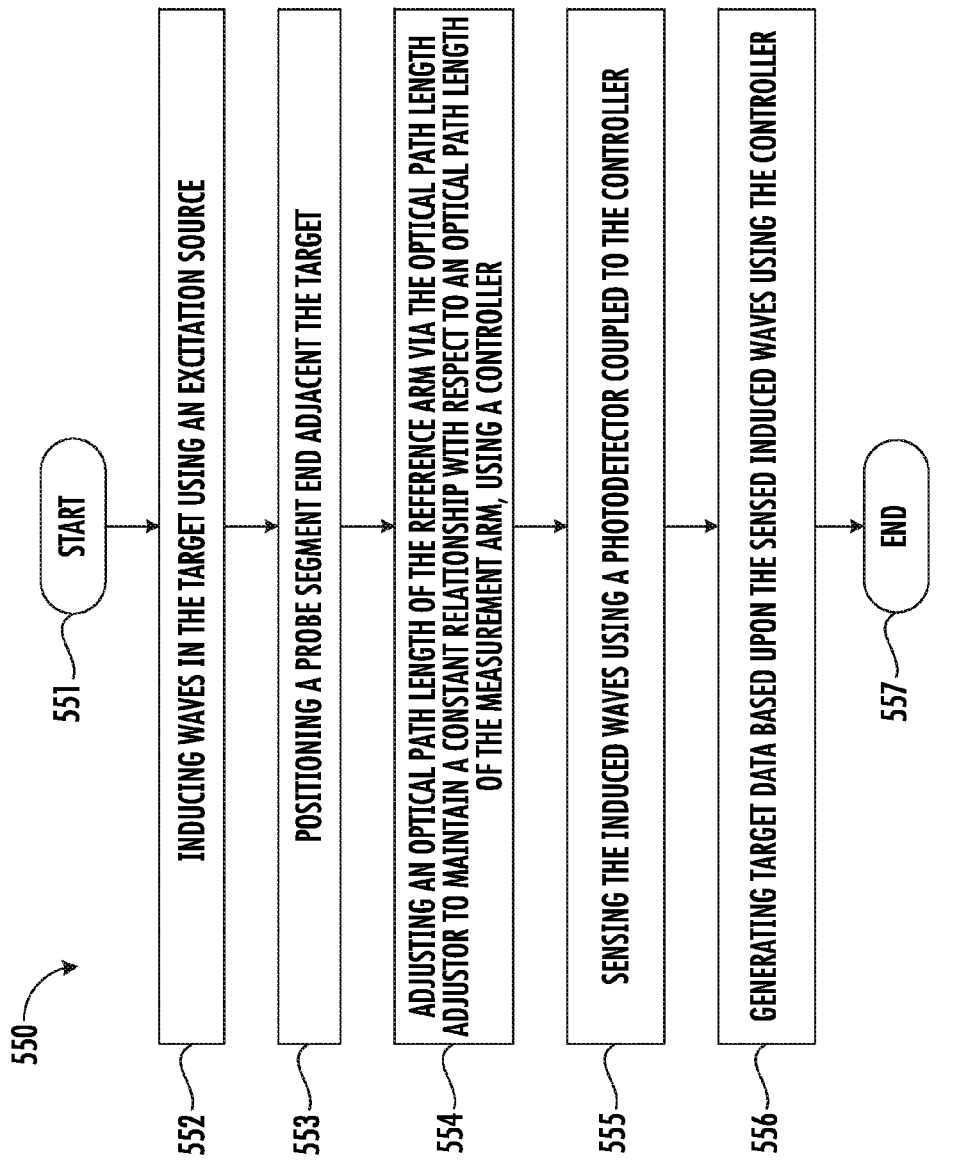
FIG. 12 is a flowchart of another method of sensing a target in accordance with the present invention.

A method of operating a sensing apparatus is now described with reference to the flowchart 550 of FIG. 12. The sensing apparatus includes an optical waveguide interferometer comprising a plurality of optical couplers and interconnecting optical fibers arranged to define a reference arm, a measurement arm, a probe segment coupled to the reference arm and the measurement arm and having a probe segment end, and an optical path length adjustor coupled to the reference arm.

After the start of the method (Block 551), the waves are induced in a target using an excitation source (Block 552). Then, a probe segment end is positioned adjacent the target (Block 553).

An optical path length of the reference arm is then adjusted via the optical path length adjustor to maintain a constant relationship with respect to an optical path length of the measurement arm, using a controller (Block 554). The induced waves are then sensed using a photodetector coupled to the controller (Block 555). Target data is then generated based upon the sensed induced waves, using the controller (Block 556). Block 557 indicates the end of the method.

It should be understood that the sensing apparatuses 400, 500 disclosed above may include an array of excitation sources 404, 504, and an array of optical waveguide interferometers 409, 509.

Figure 13:
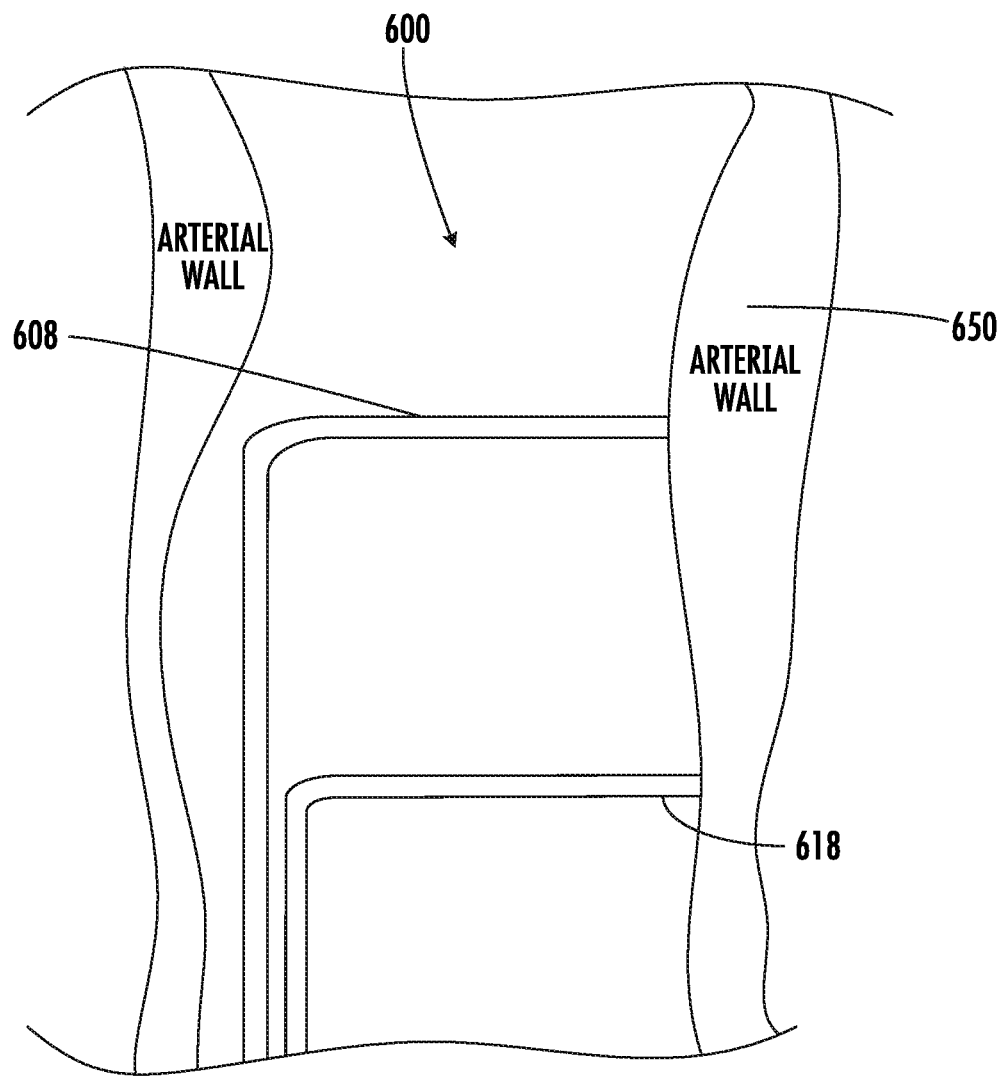
FIG. 13 is a partial schematic sectional view of a biological sensing apparatus sensing an arterial wall in accordance with the present invention.

The sensing apparatuses 400, 500 disclosed herein are useful in a wide variety of applications. For example, they may be useful in medical imaging systems, for sensing and imaging body parts. For example, the optical fibers 406, 408, 506, 508 of the excitation source and reference light source 410, 510 may be inserted into arteries, in order to image those arteries or measure the thickness thereof, or may be inserted into a trachea in order to image various components of the digestive system of a patient. Shown in FIG. 13 is an embodiment where the sensing apparatus 600 includes optical fibers 608 and 618 (similar to the sensing apparatuses 400 and 500 disclosed above) is a biological sensing device, and the target is an artery having an arterial wall 650. Here, the controller will generate anatomical data about the arterial wall 650, such as a thickness or density of the arterial wall. Those skilled in the art will appreciate that any biological sample or body part may be sensed using this sensing apparatus 600.

Figure 14:
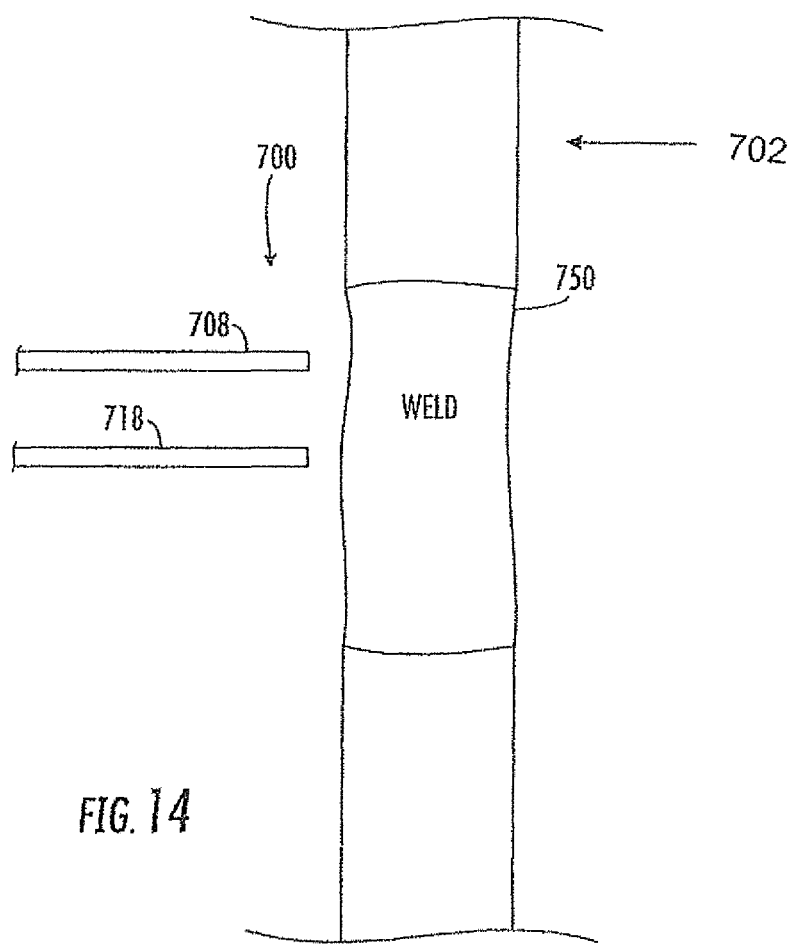
FIG. 14 is a partial schematic sectional view of a material inspection apparatus sensing a weld in accordance with the present invention.

In addition, the sensing apparatuses 400, 500 may be used for materials inspection. For example, small welds, or welds in inaccessible places, may be inspected using the sensing apparatuses 400, 500. Wire bonds in electronic devices may be inspected using the sensing apparatuses 400, 500. Hydraulic lines, such as those used in avionics systems of aircraft, or brake lines of a motor vehicle, may be inspected using the sensing apparatuses 400, 500. Shown in FIG. 14 is an embodiment where the sensing apparatus 700 includes optical fibers 708 and 718 (similar to the sensing apparatuses disclosed above) is a material inspection device, and the target 702 is a workpiece having a weld 750 to be inspected. Here, the controller will generate material data about the material weld 750, such as a thickness, density, or composition of the weld 750. Of course, this material inspection device 700 need not be limited to weld inspection and may be used to sense or inspect any sort of workpiece.

It should be understood that the specific use examples given above are by no means limiting, and that those of skill in the art will appreciate that the sensing apparatuses 400, 500, 600, 700 may be useful in an unlimited number of fields.

Other details of such sensing apparatuses 10 may be found in co-pending applications INTERFEROMETRIC SENSING APPARATUS INCLUDING ADJUSTABLE COUPLING AND ASSOCIATED METHODS, U.S. Ser. No. 13/102,619 filed May 6, 2011, now U.S. Patent Application Publication No. 2012/0281227 published Nov. 8, 2012; INTERFEROMETRIC BIOMETRIC SENSING APPARATUS INCLUDING ADJUSTABLE COUPLING AND ASSOCIATED METHODS, U.S. Ser. No. 13/102,654 filed May 6, 2011, now U.S. Patent Application Publication No. 2012/0281228 published Nov. 8, 2012; INTERFEROMETRIC SENSING APPARATUS INCLUDING ADJUSTABLE REFERENCE ARM AND ASSOCIATED METHODS, U.S. Ser. No. 13/102,712 filed May 6, 2011, now U.S. Patent Application Publication No. 2012/0281230 published Nov. 8, 2012; INTERFEROMETRIC BIOLOGICAL SENSING APPARATUS INCLUDING ADJUSTABLE REFERENCE ARM AND ASSOCIATED METHODS, U.S. Ser. No. 13/102,732 filed May 6, 2011, now U.S. Patent Application Publication No. 2012/0281231 published Nov. 8, 2012; and INTERFEROMETRIC MATERIAL SENSING APPARATUS INCLUDING ADJUSTABLE REFERENCE ARM AND ASSOCIATED METHODS, U.S. Ser. No. 13/102,755 filed May 6, 2011, now U.S. Patent Application Publication No. 2012/0281232 published Nov. 8, 2012, the entire disclosures of which are hereby incorporated by reference.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A material sensing apparatus comprising:
an excitation source configured to induce waves in a workpiece; and
an optical waveguide interferometer configured to sense the induced waves in the workpiece and comprising
a laser source,
a probe segment having a probe segment end to be positioned adjacent the workpiece and defining a gap therebetween,
a photodetector,
an optical coupler operatively connecting said laser source, said photodetector, and said probe segment, and
a controller coupled to said laser source and said photodetector, and configured to
adjust the wavelength of said laser source so that a multiple of the wavelength equals the gap between the probe segment end and the workpiece, and
generate workpiece data based upon the sensed induced waves.

2. The material sensing apparatus of claim 1, wherein said controller generates the workpiece data to represent at least one of a density, a thickness, and a composition of the workpiece.

3. The material sensing apparatus of claim 1, wherein said probe end comprises an optical fiber with an angled endface.

4. The material sensing apparatus of claim 1, wherein said excitation source comprises at least one pulsed laser.

5. A material sensing apparatus comprising:
an excitation source configured to induce waves in a workpiece; and
an optical waveguide interferometer configured to sense the induced waves in the workpiece and comprising
a laser source,
a probe segment having a probe segment end comprising an optical fiber with an angled endface to be positioned adjacent the workpiece and defining a gap therebetween,
a photodetector,
an optical coupler operatively connecting said laser source, said photodetector, and said probe segment, and
a controller coupled to said laser source and said photodetector, and configured to adjust the wavelength of said laser source so that a multiple of the wavelength equals the gap between the probe segment end and the workpiece, and generate workpiece data based upon the sensed induced waves.

6. The material sensing apparatus of claim 5, wherein said controller generates the workpiece data to represent at least one of a density, a thickness, and a composition of the workpiece.

7. The material sensing apparatus of claim 5, wherein said excitation source comprises at least one pulsed laser.

8. A method of sensing a workpiece using an optical waveguide interferometer comprising a laser source, a probe segment having a probe segment end to be positioned adjacent the workpiece and defining a gap therebetween, and an optical coupler operatively connecting said laser source and said probe segment, the method comprising:

inducing waves in the workpiece using an excitation source;

sensing the induced waves in the workpiece using the optical waveguide interferometer;

adjusting the wavelength of said laser source so that a multiple of the wavelength equals the gap between the probe segment end and the workpiece using a controller; and generating workpiece data based upon the sensed induced waves, using the controller and a photodetector coupled thereto.

9. The method of claim 8, wherein the workpiece data is generated to represent at least one of a density, a composition, and a thickness of the workpiece.

10. The method of claim 8, wherein the probe end comprises an optical fiber with an angled endface.

11. The method of claim 8, wherein the excitation source comprises at least one pulsed laser.

\* \* \* \* \*